(12) United States Patent
Agut Sanchez et al.

(10) Patent No.: US 9,233,126 B2
(45) Date of Patent: Jan. 12, 2016

(54) PLATELET-RICH PLASMA COMPOSITIONS

(71) Applicant: QUIMERA INGENIERIA BIOMEDICA, S.L., Hospitalet de Llobregat (ES)

(72) Inventors: Julian Agut Sanchez, Sant Caugat del Valles (ES); Carlos Fernandez Navarro, Rubi (ES); Joan Cos Trullas, Igualada (ES); Laura Ocana Safont, Lleida (ES); Elsa Genove Corominas, Calvia (ES)

(73) Assignee: OPKO LAB EUROPE SL, Hospitalet de Llobregat (ES)

( * ) Notice: Subject to any disclaimer, the term of this patent is extended or adjusted under 35 U.S.C. 154(b) by 184 days.

(21) Appl. No.: 13/766,206

(22) Filed: Feb. 13, 2013

(65) Prior Publication Data

US 2013/0216626 A1 Aug. 22, 2013

(30) Foreign Application Priority Data

Feb. 17, 2012 (EP) .................................... 12155924

(51) Int. Cl.

| | | |
|---|---|---|
| *A61P 19/02* | (2006.01) | |
| *A61P 19/04* | (2006.01) | |
| *A61K 35/19* | (2015.01) | |
| *A61K 38/18* | (2006.01) | |
| *A61K 35/16* | (2015.01) | |
| *A61K 9/00* | (2006.01) | |
| *A61K 9/19* | (2006.01) | |
| *A61K 9/20* | (2006.01) | |
| *A61K 9/48* | (2006.01) | |

(52) U.S. Cl.
CPC ............... *A61K 35/19* (2013.01); *A61K 9/0095* (2013.01); *A61K 9/19* (2013.01); *A61K 9/2018* (2013.01); *A61K 9/2054* (2013.01); *A61K 9/4858* (2013.01); *A61K 9/4866* (2013.01); *A61K 35/16* (2013.01); *A61K 38/18* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01)

(58) Field of Classification Search
IPC .............................................. A61P 19/02,19/04
See application file for complete search history.

(56) References Cited

U.S. PATENT DOCUMENTS

| | | | |
|---|---|---|---|
| 2006/0035383 A1* | 2/2006 | Ho et al. .......................... | 436/69 |
| 2007/0048328 A1 | 3/2007 | Nakao | |
| 2010/0183561 A1* | 7/2010 | Sakthivel et al. ............ | 424/93.7 |
| 2012/0230968 A1* | 9/2012 | Worden, Sr. ............... | 424/93.72 |

FOREIGN PATENT DOCUMENTS

| | | |
|---|---|---|
| WO | 2006/015178 A2 | 2/2006 |
| WO | 2010/064267 A1 | 6/2010 |

OTHER PUBLICATIONS

Alio et al. Symtomatic Dry Eye Treatment With Autologous Platelet-Rich Plamsa; Ophthalmic Research, vol. 39 (2007) pp. 124-129.*
Petrungaro, P.S. Using Platelet-Rich Plasma to Accelerate Soft Tissue Maturation in Esthetic Periodontal Surgery; Compendium of Continuing Education in Dentistry, vol. 22, No. 9 (2001) pp. 1-10.*
Akeda et al. Platelet-Rich Plasma Stimulates Porcine Articular Chondrocyte Proliferation and Matrix Biosynthesis; Osteoarthritis and Cartilage, vol. 14 (2006) pp. 1272-1280.*
Arnoczky, S.P. et al., "What is Platelet-Rich Plasma?," Operative Techniques in Sports Medicine, vol. 19, No. 3, Dec. 29, 2010, pp. 142-148, © 2011 Elsevier Inc.
Ogundipe, O.K. et al., "Can Autologous Platelet-Rich Plasma Gel Enhance Healing After Surgical Extraction of Mandibular Third Molars?," Journal of Oral and Maxillofacial Surgery, vol. 69, No. 9, May 7, 2011, pp. 2305-2310, © American Association of Oral and Maxillofacial Surgeons.
Kon, Elizaveta et al., "Platelet-Rich Plasma Intra-Articular Injection Versus Hyaluronic Acid Viscosupplementation as Treatments for Cartilage Pathology: From Early Degeneration to Osteoarthritis," Arthroscopy: The Journal of Arthroscopic and Related Surgery, vol. 27, No. 11, Nov. 2011, pp. 1490-15.01, © 2011 by the Arthroscopy Association of North America.
Saito, M. et al., Poster Presentations, "428 The Preventive Effect of Platelet-Rich Plasma and Biodegradable Gelatin Hydrogel Microspheres on Experimental Osteoarthritis in the Rabbit Knee," Osteoarthritis and Cartilage, Bailliere Tindall, London, GB, vol. 15, Dec. 1, 2007, p. C232, 1 page.
EP Search Report dated Jul. 6, 2012, Application No. 12155924.9-2107, Applicant: Quimera Ingenieria Biomedica, S.L., 10 pages.

* cited by examiner

*Primary Examiner* — Kagnew H Gebreyesus
*Assistant Examiner* — Paul Martin
(74) *Attorney, Agent, or Firm* — Rothwell, Figg, Ernst & Manbeck P.C.

(57) ABSTRACT

The present invention relates to a method of treating functional disability and/or pain associated with joints, tendons or connective tissue diseases, disorders or injuries comprising oral administration of a composition comprising heterologous platelet-rich plasma. The invention also relates to pharmaceutical compositions and nutritional compositions comprising heterologous platelet-rich plasma and uses thereof.

14 Claims, 4 Drawing Sheets

PLATELET-RICH PLASMA COMPOSITIONS

TECHNICAL FIELD OF THE INVENTION

The present invention relates to a method of treating functional disability and/or pain associated with joints, tendons or connective tissue diseases, disorders or injuries comprising oral administration of a composition comprising heterologous platelet-rich plasma. The invention also relates to pharmaceutical compositions and nutritional compositions comprising heterologous platelet-rich plasma and uses thereof.

BACKGROUND OF THE INVENTION

Platelet-rich plasma (PRP) is a blood-derived product that is rich in platelets. PRP is typically obtained from the blood of a patient and is used in regenerative medicine.

Platelets play a fundamental role in hemostasis and are a natural source of growth factors. The release of these growth factors is triggered by the activation of platelets that can be initiated by a variety of substances or stimuli such as thrombin, calcium chloride or collagen. Growth factors are naturally occurring proteins capable of stimulating cell proliferation and differentiation. Studies have found that growth factors are important in different stages of the wound-healing cascade and greatly influence mitogenic and cellular differentiation activities (Pierce et al., *Proc Natl. Acad Sci. U.S.A.* 86(7), 2229-2233 (1989) and *J. Cell Biol.* 109(1), 429-440 (1989) and D. L. Steed et al., *Surg. Clin. North Am.* 77, 575-586 (1997)). Therefore, growth factors are potentially useful for specifically promoting wound healing and tissue repair. PRP generally may include one or more of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4) and hepatocyte growth factors (HGF).

In particular, transforming growth factors (TGF) present in PRP specially include those of the TGF-β family. TGF-β is a protein that controls proliferation, differentiation, and other functions of cells. It can also act as a negative autocrine growth factor. TGF-β is known to activate fibroblasts to form procollagen resulting in collagen deposition within the wound. Other growth factors such as PDGF are activators of collagenase during wound healing allowing reshaping of collagen for wound strength.

PRP has many medical applications, primarily in constructive oral surgery and as part of a composition used as a surgical adhesive. PRP has been used to form a fibrin tissue adhesive through activation of the PRP using thrombin and calcium, which activate the platelets to release their contents such as cytokinins and other growth factors. For example, U.S. Pat. No. 6,322,785 discloses an autologous platelet gel comprising PRP for bone graft and dental implant applications.

The use of PRP has expanded into novel applications, such as bio-tissue engineering or autologous and allogenic tissue grafts, as well soft tissue regeneration (Oikarinen et al., *Dent. Traumatol.* 19, 19-29 (2003)). These applications include PRP as part of a composition for wound healing (U.S. Pat. No. 5,599,558) and tissue repair (U.S. Pat. No. 6,811,777), for use as a tissue sealant (U.S. Pat. No. 5,585,007) or in combination with a biopolymer to temporarily block arteries and veins (U.S. Pat. No. 5,614,204). Moreover, WO 2011/127071 relates to PRP formulations and their use in treating ischemic injury, particularly damaged connective tissue, cardiac tissue and lung tissue.

U.S. Pat. No. 6,811,777 discloses a platelet-rich plasma composition for treating injured tissue such as connective tissue, cardiac muscle, skeletal muscle, disc material, vertebral body, brain, spinal cord and vascular tissue by introducing the platelet-rich plasma composition into and around the site of a tissue injury.

The most expeditious source of PRP is from blood extracted from a patient, the PRP may thus be obtained and activated for use on the same patient; methods of using a patient's own blood are called "autologous" or "autogenic" donor methods. When the blood is donated by a human, but not the same human being treated, is called "homologous". Homologous sources of PRP may be biologically or immunologically incompatible with the patient and can imply a potential risk of contamination with hepatitis and HIV contaminants. Autologous PRP has several safety advantages. For example, since PRP is generally a byproduct of the patient's own blood, disease transmission or immunological reactions are not an issue. However, patients with complex systemic diseases can affect the concentration of growth factors in their blood and in any of the blood-derived preparations, therefore will not benefit from the advantages of this type of treatments. Furthermore, certain treatments required platelet compositions which must be prepared on a daily basis and thus require regular blood withdrawal from the patient.

In view of the above, "heterologous" sources of PRP (from a foreign specie) may be of interest since they can provide a reliable, largely available and highly reproducible source of raw material. For example, porcine blood is less likely to carry a human viral infectious risk (HIV, hepatitis, etc), the production of growth factors is nearly 100% identical to their human counterparts and, is a source of efficient and constant concentration of growth factors. Additionally, in many countries, slaughter blood is discarded as waste material for lack of possibilities of using the blood.

Thus, it would be highly desirable to obtain composition comprising PRP without the need of a patient's own blood and from a more available, accessible and economical source such as porcine blood.

Furthermore, the use of autologous PRP for treating patients affected by knee degeneration with PRP intra-articular injections has been described by G. Filardo et al., *Knee Surg. Sports Traumatol. Arthrosc.* 19(4), 528-35 (2011). Osteoarthritis is a joint disease with a high incidence and prevalence in the population. The main symptom is pain, causing loss of ability and often stiffness. It has no cure and palliative treatments such as administration of analgesics and anti-inflammatories are mainly used to treat the symptoms. Indeed, sustained release of growth factors contained in PRP has preventive effects against osteoarthritis progression. The treatment with PRP injections can reduce pain and improve knee function and quality of life but with a short-term efficacy. These preventive effects appear to be due to stimulation of cartilage matrix metabolism caused by the growth factors contained in PRP (Saito et al., *Clin. Exp. Rheumatol.* 27(2), 201-7 (2009)).

PCT/IB2008/001916 discloses a method for the treatment of articular diseases or articular pain, which comprises the infiltration in the joint of a compound that comprises at least one autologous blood-derived substance.

As explained above, growth factors are known to be useful for promoting wound healing and tissue repair. The addition of exogenous growth factors to wound has been shown to increase the rate at which the wound is closed, the number of cells in the healing area, the growth of blood vessels and the strength of the scar (Carter et al., *Biolog. and Clinical Implications* 303 (1988)).

A platelet-derived wound healing formula in the form of a salve or ointment for topical application has been described by Knighton et al., *Ann. Surg.* 204, 322-330 (1986).

As disclosed in the above mentioned prior art, most biologicals, such as peptides and protein drugs, are currently used as parenteral formulations because of their poor oral bioavailability. The main reasons for the low oral bioavailability of biologicals are their unfavourable physicochemical properties, which include enzymatic degradation, poor intestinal membrane permeability and large molecular size (R. I. Mahato et al., *Crit. Rev. Ther. Drug Carrier Syst.* 20, 153-214 (2003) and J. H. Hamman et al., *Bio Drugs* 19, 165-177 (2005)). Platelet-rich plasma (PRP) contains high levels of biological entities, such as platelets and growth factors, therefore autologous PRP formulations are typically parenterally administered.

To date, there have been no reports of successful oral administration of PRP or successful use of heterologous PRP in vivo orally administered to develop the therapeutical effects described in the present invention.

The inventors of the present invention have surprisingly found that growth factor TGF-$\beta$1 is not degraded under gastric and gastrointestinal conditions and consequently TGF-$\beta$1 levels are not affected by digestion. This result was totally unexpected, especially in view of the poor oral bioavailability shown by biologicals.

EXPLANATION OF THE INVENTION

The inventors have surprisingly found that compositions comprising heterologous platelet-rich plasma can be formulated for oral administration and are useful in the treatment of several types of tissue diseases, disorders or injuries.

Thus, the present invention relates to a method of treating functional disability and/or pain associated with joints, tendons or connective tissue diseases, disorders or injuries comprising oral administration of a composition comprising heterologous platelet-rich plasma (PRP). In particular, an object of the present invention is to provide a composition comprising heterologous PRP which can be administered orally and is effective in the treatment or prevention of functional disability and/or pain associated with osteoarthritis.

Additionally, the present invention further discloses a pharmaceutical composition and a nutritional composition or nutritional supplement for oral administration comprising heterologous platelet-rich plasma.

Accordingly, in its broadest aspect, the present invention relates to a method of treating functional disability and/or pain associated with joints, tendons or connective tissue diseases, disorders or injuries comprising orally administering a composition comprising heterologous platelet-rich plasma (PRP), in an amount effective to treat functional disability and/or pain associated with joints, tendons or connective tissue diseases, disorders or injuries. Examples of such joint, tendons or connective tissue diseases, disorders or injuries include, without limitation, joint damage, injured tendons, arthritis, osteochondral lesions, osteoarthritis, tendonitis, tenosynovitis, bursitis and ligament injuries. Preferably, said heterologous platelet-rich plasma is from whole blood of animals. More preferably, whole blood of cattle or pigs is used. Even more preferably, the orally administered composition for the treatment of functional disability and/or pain associated with joints, tendons or connective tissue diseases, disorders or injuries comprises heterologous platelet-rich plasma of porcine origin.

In one preferred embodiment, the invention also provides a method of treating functional disability and/or pain associated with osteoarthritis comprising orally administering a composition comprising heterologous platelet-rich plasma. Preferably, said heterologous platelet-rich plasma is from whole blood of animals. More preferably, whole blood of cattle or pigs is used. Even more preferably, the heterologous platelet-rich plasma is of porcine origin.

In another embodiment, the method of treating functional disability and/or pain associated with joints, tendons or connective tissue diseases, disorders or injuries comprises orally administering a composition comprising heterologous platelet-rich plasma, wherein the composition further comprises growth factors. Preferably, said composition comprises growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof. More preferably, the growth factors are transforming growth factors (TGF), platelet-derived growth factors (PDGF) fibroblast growth factors (FGF) or mixtures thereof. Even more preferably, the growth factors are selected from the group consisting of transforming growth factors $\beta$ (TGF-$\beta$), platelet-derived growth factors BB (PDGF-BB), basic fibroblast growth factors (bFGF) and mixtures thereof. Even more preferably, the growth factors are transforming growth factors $\beta$1 (TGF-$\beta$1).

In another embodiment, the invention also includes a method of treating functional disability and/or pain associated with osteoarthritis comprising orally administering a composition comprising heterologous platelet-rich plasma, wherein the composition further comprises growth factors. Preferably, said composition comprises growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof. More preferably, the growth factors are transforming growth factors (TGF), platelet-derived growth factors (PDGF) fibroblast growth factors (FGF) or mixtures thereof. Even more preferably, the growth factors are selected from the group consisting of transforming growth factors $\beta$ (TGF-$\beta$), platelet-derived growth factors BB (PDGF-BB), basic fibroblast growth factors (bFGF) and mixtures thereof. Even more preferably, the growth factors are transforming growth factors $\beta$1 (TGF-$\beta$1).

For oral administration, the composition comprising heterologous platelet-rich plasma can be incorporated into a formulation that might includes one or more agents, carriers or excipients such as inert diluents, disintegrating agents, binding agents, lubricating agents, sweetening agents, flavouring agents, colouring agents and preserving agents in order to provide palatable preparations. The formulation can be orally delivered in the form of enclosed gelatin capsules or compressed tablets. Capsules and tablets can be prepared in any conventional techniques. Tablets can contain the composition according to invention in admixture with non-toxic acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, sodium carboxymethylcellulose, crosspovidone, sodium starch glycolate or alginic acid; lubricants (e.g., magnesium stearate, silicon dioxide), and binding agents, for example magnesium stearate, stearic acid, lactose monohydrate, microcrystalline cellulose or talc. The capsules and tablets may be coated with various coatings known in the art to modify the flavours, tastes, colours, and shapes of the capsules and tablets. The capsules and tablets can also be coated by known techniques to delay disintegration and adsorption in the gastrointestinal tract, thereby providing a sustained action over a longer period. For example, a time delay material such as glyceryl monostearate or glyceryl distearate may be employed. Formulations for oral use may also be presented as hard gelatin capsules wherein the composition is mixed with an inert solid diluent, for example, calcium carbonate, calcium phosphate or kaolin, or as soft gelatin capsules wherein the composition is mixed with water or an oil medium, for example peanut oil, liquid paraffin or olive oil. Suitable oral formulations can also be in the form of suspension, syrup, chewing gum, wafer, elixir, and the like. If desired, conventional agents for modifying flavours, tastes, colours, and shapes of the special forms can also be included. In addition, for convenient administration by enteral feeding tube in patients unable to swallow, the composition can be dissolved in an acceptable lipophilic vegetable oil vehicle such as olive oil, corn oil and safflower oil.

The composition comprising heterologous PRP for oral administration may also be an aqueous suspension containing said composition in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products. The aqueous suspensions may also contain one or more preservatives, for example ethyl, or n-propyl p-hydroxybenzoate, one or more colouring agents, one or more flavouring agents, and one or more sweetening agents, such as sucrose, fructose or saccharin.

Dispersible powders and granules suitable for preparation of an aqueous suspension by the addition of water provide the composition of the present invention in admixture with a dispersing or wetting agent, a suspending agent and one or more preservatives. Suitable dispersing or wetting agents and suspending agents are exemplified by those already mentioned above. Additional excipients, for example, sweetening, flavouring and colouring agents, may also be present.

Accordingly, in another embodiment of the present invention, the composition comprising heterologous platelet-rich plasma described herein is in solid oral dosage form. Preferably, said composition is in the form of granules, a tablet, a capsule, a powder or a dry powder which can be suspended and reconstituted in water.

In another embodiment, the composition above described is administered orally in a dose ranging from 0.2 g to 5 g per day.

In another embodiment, the composition can be administered orally once or more per day for one year or longer.

In another embodiment, the composition for oral administration comprises between 1 and 25 wt % of heterologous PRP with respect to the total weight of the composition. Preferably, between 1 and 25 wt % of heterologous PRP of porcine origin with respect to the total weight of the composition.

In another embodiment, the composition for oral administration as described herein, further comprises between 1 and 25 wt % of a bulking agent and between 50 and 98 wt % of at least one excipient or carrier. Preferably, the excipient or carrier is selected from the group consisting of binder agents, fillers, diluents, film forming agents, lubricants, glidants, disintegrants, preservatives, stabilizers, antioxidants, coatings, antiadherents, flavours, sweeteners, colours and mixtures thereof. Examples of such bulking agents include without limitation, mannitol, sorbitol, fructose, glucose, mannose, sorbose, xylose, maltose, lactose, sucrose, dextran, inositol, dulcitol, xylitol, arabitol, trehalose, arginine, glycine, histidine, and polyethylene glycol. Without limitation, the excipient or carrier may be one or more of the following compounds: microcrystalline cellulose, tricalcium phosphate, lactose monohydrate, hydroxypropylcellulose, sodium croscarmellose, sodium starch, colloidal silica, Aerosil 200, magnesium stearate, fructose, pineapple flavour, sodium ascorbate and mixtures thereof.

In another aspect of the invention, the present invention relates to a pharmaceutical composition for oral administration comprising heterologous platelet-rich plasma (PRP) and at least one pharmaceutically acceptable excipient. Preferably, said platelet-rich plasma is from whole blood of animals. More preferably, whole blood of cattle or pigs is used.

In another embodiment, the pharmaceutical composition for oral administration comprises heterologous platelet-rich plasma of porcine origin and at least one pharmaceutically acceptable excipient, wherein the heterologous platelet-rich plasma has not been chemically activated and is in solid form.

Accordingly, in another embodiment of the present invention, the pharmaceutical composition comprising heterologous platelet-rich plasma described herein is in solid oral dosage form. Preferably, said pharmaceutical composition is in the form of granules, a tablet, a capsule, a powder or a dry powder which can be suspended and reconstituted in water.

In another embodiment, the pharmaceutical composition comprising heterologous platelet-rich plasma further comprises growth factors. Preferably, said pharmaceutical composition comprises growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof. More preferably, the growth factors are transforming growth factors (TGF), platelet-derived growth factors (PDGF), fibroblast growth factors (FGF) or mixtures thereof. Even more preferably, the growth factors are selected from the group consisting of transforming growth factors β (TGF-β), platelet-derived growth factors BB (PDGF-BB), basic fibroblast growth factors (bFGF) and mixtures thereof. Even more preferably, the growth factors are transforming growth factors β1 (TGF-β1).

In one embodiment, the pharmaceutical composition for oral administration comprises heterologous platelet-rich plasma of porcine origin in solid form which has not been chemically activated, growth factors and at least one pharmaceutically acceptable excipient.

In one embodiment, the pharmaceutical composition comprising heterologous platelet-rich plasma as described herein can be used as a medicament.

In another embodiment of the invention, the pharmaceutical composition for oral administration comprising heterologous PRP as described herein above, can be used in the treatment or prevention of functional disability and/or pain associated with joints, tendons or connective tissue diseases, disorders or injuries. Preferably, said platelet-rich plasma is of porcine origin. Examples of such joint, tendons or connective tissue diseases, disorders or injuries include, without limitation, joint damage, injured tendons, arthritis, osteochondral lesions, osteoarthritis, tendonitis, tenosynovitis, bursitis and ligament injuries.

Accordingly, in one preferred embodiment, the invention provides an orally administered pharmaceutical composition comprising heterologous platelet-rich plasma for use in the treatment or prevention of functional disability and/or pain associated with osteoarthritis. Preferably, said pharmaceutical composition comprises heterologous platelet-rich plasma of porcine origin.

In another embodiment, the pharmaceutical composition is administered orally in a dose ranging from 0.2 g to 5 g per day.

In another embodiment, the pharmaceutical composition can be administered orally once or more per day for one year or longer.

Additionally, in another embodiment, the pharmaceutical composition for oral administration comprising heterologous PRP of the present invention can be used for promoting wound healing or tissue regeneration. The wound can be, for example, an internal wound or a cutaneous wound and can include, but is not limited to, cutaneous wound (e.g., a pressure ulcer, a venous stasis ulcer, a diabetic ulcer, an arterial ulcer, an injury wound, a burn wound, a complex soft tissue wound, a failed skin graft or flap, a radiation-induced wound, or a gangrenous wound) or an internal wound (e.g., a wound under or below the skin). Internal wounds can include, but are not limited to, a contusion, a fracture, a fistula, an ulcer, or an injury wound of an internal organ. Preferably, said orally administered pharmaceutical composition comprises heterologous platelet-rich plasma of porcine origin.

In another embodiment, the pharmaceutical composition for oral administration comprising heterologous PRP according to the invention can be used in the treatment of peptic ulcers (including esophageal, stomach and duodenal ulcers), ulcerative colitis (colon and rectum) and Crohn's disease. Preferably, the orally administered pharmaceutical composition for use in the treatment of peptic ulcers, ulcerative colitis and Crohn's disease comprises heterologous PRP from porcine blood.

In another embodiment, the pharmaceutical composition for oral administration comprising heterologous PRP according to the invention can be used in the treatment or prevention of skin aging.

In another embodiment, the pharmaceutical composition comprises between 1 and 25 wt % of heterologous PRP with respect to the total weight of the pharmaceutical composition. Preferably, said pharmaceutical composition comprises between 1 and 25 wt % of heterologous PRP of porcine origin.

In another embodiment, the pharmaceutical composition for oral administration as described herein, further comprises between 1 and 25 wt % of a bulking agent and between 50 and 98 wt % of at least one pharmaceutically acceptable excipient or carrier with respect to the total weight of the composition.

The pharmaceutical composition comprising heterologous platelet-rich plasma of the present invention may be used in conjunction with other known therapies, compounds or formulations. For example, said pharmaceutical composition may be orally administered in combination with one or more other agents selected from antiinflammatories, antirheumatics, steroids, chondrogenic stimulating factors, monosaccharides, oligosaccharides and polysaccharides (e.g. glucosamine), glycosaminoglycans (e.g. hyaluronic acid and chondroitin sulfate), proteins (e.g. hydrolized collagen), essential fatty acids and antioxidants either separately or in a single formulation.

In another aspect, the present invention further provides a cosmetic composition orally administered comprising heterologous PRP. Preferably, the cosmetic composition orally administered comprises heterologous platelet-rich plasma of porcine origin.

In one embodiment, the cosmetic composition as described herein, further comprises growth factors. Preferably, said cosmetic composition comprises growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof. More preferably, the growth factors are transforming growth factors (TGF), platelet-derived growth factors (PDGF), fibroblast growth factors (FGF) or mixtures thereof. Even more preferably, the growth factors are selected from the group consisting of transforming growth factors β (TGF-β), platelet-derived growth factors BB (PDGF-BB), basic fibroblast growth factors (bFGF) and mixtures thereof. Even more preferably, the growth factors are transforming growth factors β1 (TGF-β1).

In another aspect, the present invention relates to the use of an orally administered cosmetic composition comprising heterologous platelet-rich plasma for preventing, retarding or treating skin aging. Preferably, said heterologous PRP is porcine PRP.

In another aspect, the present invention provides a nutritional composition or nutritional supplement for oral administration comprising heterologous platelet-rich plasma. Preferably, the nutritional composition or nutritional supplement comprises heterologous platelet-rich plasma of porcine origin.

In one embodiment, the nutritional composition or nutritional supplement for oral administration comprises heterologous platelet-rich plasma of porcine origin, wherein the heterologous platelet-rich plasma has not been chemically activated and is in solid form.

In one embodiment, the nutritional composition or nutritional supplement comprising heterologous PRP as described herein above further comprises growth factors. Preferably, said nutritional composition or nutritional supplement comprises growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF)-, platelet-derived angiogenesis factors (PDAF), platelet factors 4 (PF-4), hepatocyte growth factors (HGF) and mixtures thereof. More preferably, the growth factors are transforming growth factors (TGF), platelet-derived growth factors (PDGF), fibroblast growth factors (FGF) or mixtures thereof. Even more preferably, the growth factors are selected from the group consisting of transforming growth factors β (TGF-β), platelet-derived growth factors BB (PDGF-BB), basic fibroblast growth factors (bFGF) and mixtures thereof. Even more preferably, the growth factors are transforming growth factors β1 (TGF-β1).

In another embodiment, the orally administered nutritional composition or nutritional supplement comprising heterologous PRP as described herein, further comprises one or more acceptable additives and vehicles.

Another aspect of the invention is a process of preparing the composition comprising heterologous platelet-rich plasma describe herein above. Therefore, the present invention also relates to a process for the preparation of said composition comprising:

a) a single slow-speed centrifugation of whole animal blood to prepare a platelet-rich plasma supernatant, preferably, whole blood of cattle or pigs is used, b) adding a bulking agent to the supernatant of step a), and c) lyophilizing the supernatant solution of step b).

Therefore, the heterologous PRP composition obtained by the process described above is a solid composition of platelets with plasma and growth factors, which does not need to be chemically activated and does not clot.

The compositions comprising heterologous platelet-rich plasma for oral administration of the present invention may be for human or veterinary use. For veterinary use, the compositions as described herein are administered orally as a suitable acceptable formulation for veterinary use.

The embodiments described above are considered to be illustrative in all respects and not restrictive, the scope of the invention being indicated by the appended claims rather than by the foregoing description. Those skilled in the art will recognize that the preferred modes may be altered or amended without straying away from the true spirit and scope of the invention as defined in the enclosed claims.

BRIEF DESCRIPTION OF THE FIGURES

For the purpose of better illustrating the advantages and properties of the composition object of the invention, several graphs and images are attached as non-limiting examples.

DETAILED EXPLANATION OF THE INVENTION

Figure 1:
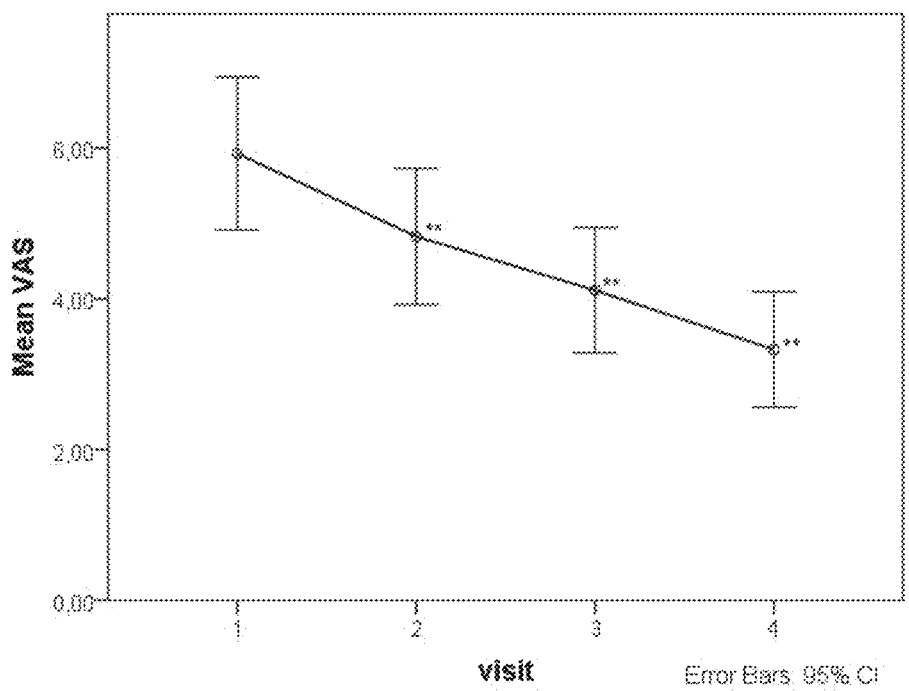
FIG. 1 shows mean VAS scores at visits 1, 2, 3 and 4, which correspond to day 0, 15, and 60 respectively. (Error bars, 95% CI, **$p<0.01$).

Heterologous sources of platelet-rich plasma can be any animal species from which is possible to obtain the required amount of blood, but most preferably are porcine. The animals intended with the present invention can basically be all animals, both young ones and adults. Preferably blood extracted in slaughter is used, and the blood comes mainly from adult animals. Examples of animals that are convenient for use in the present invention are slaughter animals and other farm animals such as cattle, pigs, sheep and goats. Preferably, whole blood of cattle or pig is used.

The porcine origin of the blood, in accordance with the present invention, guaranties: 1) a total absence of potential transmission of human viral agents (Hepatitis, HIV, etc.), 2) the production of growth factors nearly 100% identical to their human counterparts and, 3) a reliable, largely available and highly reproducible source of raw material.

Methods for preparing platelet-rich plasma have already been described in many reports. Typically, autologous PRP kits use an anti-coagulant to prevent blood from clotting and PRP is activated prior to injection resulting in a rapid growth factor release. Activation of growth factors may occur in a variety of manners, typically, by a variety of substances known as activators. For example, it is known that TGF-$\beta$1 is present in platelet granules and is released upon platelet activation with $CaCl_2$. On the contrary, in the present invention no activators are needed since the lyophilization of PRP causes a mechanical stress which breaks and releases platelets growth factors.

In the present invention, heterologous platelet-rich plasma, preferably of porcine origin, is prepared by low speed centrifugation in order to pellet and remove red blood cells and white blood cells from whole blood. The isolated platelet-rich plasma supernatant is dissolved in a bulking agent (e.g. mannitol) and then undergoes a lyophilization process.

The compositions of the present invention resulted in an improved heterologous platelet-rich plasma composition containing growth factors (Table 2). Said compositions are in solid form, have not been chemically activated and does no clot.

In particular, the levels of TGF-$\beta$ (especially the $\beta$1 isoform) were evaluated because TGF-$\beta$ promotes the production of extracellular matrix to enhance the proliferative activity of fibroblast, to stimulate biosynthesis of type I collagen and fibronectin and to induce deposition of bone matrix. On the other hand, this growth factor may inhibit osteoclast formation and bone resorption thus favouring bone formation over resorption.

As detailed below in Table 3, the results showed that TGF-$\beta$1 levels in lyophilized PRP resulted in a 4.1-fold increase compared to PRP baseline (non activated). Moreover, no differences were observed when TGF-$\beta$1 levels from lyophilized PRP (non activated) were compared with TGF-$\beta$1 levels from PRP activated with $CaCl_2$.

As explained above, oral administration of drugs is by far the most widely used route of administration. Unlike conventional small molecular drugs, oral delivery of biological drugs such as peptides, proteins or macromolecular drugs, it is generally not feasible without some sort of sophisticated pharmaceutical technology. The main reason for the low oral bioavailability of biologicals is presystemic enzymatic degradation and poor penetration of the intestinal membrane.

The inventors have surprisingly found that the compositions comprising platelet rich plasma of the present invention retain their functional and therapeutical properties when administered orally, preferably through digestive tract tissue and are subjected to the digestive environment.

To assess gastrointestinal stability of the composition comprising PRP according to the invention, TGF-β1 levels were measured under gastrointestinal and gastric conditions (see Table 1).

PRP samples were incubated under gastric and gastrointestinal conditions as previously described by E. Peña et al., *J. Agric. Food Chem.*, 52 (15), (2004). To assess gastric stability, lyophilized PRP (151 mg/mL) was incubated at pH=2.0 with porcine pepsin (PEP; Sigma Aldrich P-7000, EC 3.4.23.1 at a final concentration of 3.8 U/mL) for 50 min at 37° C. Samples were further neutralized using $NaHCO_3$ and incubated under intestinal conditions using pancreatin (PAN; Sigma-Aldrich P-1750 at a final concentration of 9.3 µg/mL) for 30 min at 37° C. to assess gastrointestinal stability.

In all cases, enzymatic treatments were stopped by placing the digested products in an ice-water bath to cool.

Control samples (without enzymatic treatment) were included (for gastric stability control: PRP at pH=2.0 for 50 min and for gastrointestinal stability control: PRP at pH=2.0 (50 min)+pH=7.0 (30 min) (Table 1).

Samples were centrifuged at 10.000×g for 30 min at 4° C. to obtain TGF-β1 soluble fraction. TGF-β1 was analyzed by ELISA following the manufacturer's instructions (Quantikine Mouse/Rat/Porcine/Canine TGF-β1; R&D Systems). Table 1 shows TGF-β1 levels in control samples (lyophilized PRP without enzymatic treatment) and in samples under gastric conditions (PEP) and gastrointestinal conditions (PEP+PAN).

TABLE 1

TGF-β1 levels (ng/mL)

| PRP sample | TGF-β1 levels (ng/mL) |
|---|---|
| initial lyophilized PRP | 5.92 |
| gastric stability control pH ~2 | 6.28 |
| gastrointestinal stability control pH ~2 + pH ~7 | 4.70 |
| gastric conditions PEP (3.8 U/mL) | 6.81 |
| gastrointestinal conditions PEP (3.8 U/mL) + PAN (9.3 µg/mL) | 6.56 |

Surprisingly, results showed that TGF-β1 levels in lyophilized PRP according to the invention were comparable and non-affected by pH or enzymatic treatment. These observations suggested that TGF-β1 present in lyophilized PRP is stable after gastrointestinal treatment.

Besides the composition, the invention also refers to the use of any of the compositions comprising heterologous PRP according to the invention for the treatment or prevention of functional disability and/or pain associated with joints, tendons or connective tissue disease, disorder or injury, particularly in the treatment of functional disability and/or pain associated with osteoarthritis. Surprisingly, the inventors have found that oral administration of the PRP composition according to the invention for 60 days is effective in the reduction of functional disability and/or pain in knee osteoarthritis patients. An improvement in the mean value of VAS and WOMAC scores was observed across the study. Most variables were significantly different from basal scores at the end of the study. These results were confirmed by the subjective evaluation of both physician and patient, who considered the treatment effective throughout the evaluation. The treatment was well tolerated and no adverse events or immune reactions were observed.

The terms "oral administration", "orally administered" or "oral delivery," as used herein, include any form of delivery of the pharmaceutical composition according to the invention to a subject or animal, wherein the composition is placed in the mouth of the subject or animal, whether or not the composition is swallowed. Thus "oral administration" includes buccal and sublingual as well as esophageal administration. The term "oral administration" in this document is associated to a systemic effect.

All percentages as used herein pertaining to listed components of the compositions according to the invention are weight percentages, calculated based on the total weight of said composition unless otherwise specified.

The following examples are provided to further illustrate the composition according to the present invention and other compositions comprising heterologous PRP. The examples provided below are illustrative and are not intended to limit the scope of the claimed invention.

Example 1

Platelet-Rich Plasma (PRP) Preparation a) Blood Collection

For experimental purposes 24 large white pigs intended for human consumption were used. A total of 1968.20±322.66 mL of porcine blood was collected by terminal bleeding of the jugular vein. The blood was stored in sterile containers and was mixed with dextrose-citrate in a 1:9 (1 dextrose citrate:9 blood) v/v ratio. Samples were kept at 4° C. until further processing.

b) Platelet Count

Platelet counting analysis from blood and plasma were performed using a ABX Pentra DX 120 SPS (HORIBA Medical). Data showed a total of $4.18 \pm 1.54 \times 10^{11}$ platelets/pig (range: $2.04\text{-}8.04 \times 10^{11}$) in blood and $1.51 \pm 0.87 \times 10^{11}$ platelets/pig (range: $0.48\text{-}3.35 \times 10^{11}$) in plasma (recovery: 36.12%).

c) Process for Obtaining PRP

The collected sterile porcine blood was centrifuged at 780 g for 10 min at room temperature to remove red blood cells and lymphocytes. The supernatant (776.96±184.15 mL of PRP/pig) was collected and mannitol was added as a bulking agent at a final concentration of 8% (w/v). The solution was stirred for 15-30 minutes before lyophilization.

d) Lyophilization of Porcine Plasma

A pool of 4700 ml of porcine plasma with mannitol was used in each lyophilization process. This process was carried out using a TELSTAR L-3 model. Porcine plasma was frozen at −56° C. The sublimation process was performed at 30-32° C. and then, the product was dried at 26-32° C. After lyophilization 3050.23 g of a solid product was obtained with a total solid content of 70.48% protein, 18.81% carbohydrates, 0.05% fatty acids, 5.80% moisture and 4.86% ashes.

e) Measurement of Growth Factors

In order to quantify growth factors levels (PDGF-BB, FGF-basic and TGF-β1 levels) in lyophilized PRP, samples were reconstituted with Dulbecco's modified phosphate buffer (PBS) without calcium and magnesium (84.5-92 mg PRP/mL of PBS) and then centrifuged at 10000 g (4° C.) for 10 minutes to remove cell debris. After centrifugation, the supernatants were aspirated and used to quantify the growth factors levels by ELISA kits following the manufacturer's instructions (Quantikine ELISA human PDGF-BB, R&D Systems; Quantikine ELISA human FGF-Basic, R&D Systems and Quantikine Mouse/Rat/Porcine/Canine TGF-β1; R&D Systems). Table 2 shows the growth factors levels in lyophilized PRP.

TABLE 2

PDGF-BB, FGF-basic and TGF-β1 levels
(ng/mL) in lyophilized PRP

| Growth factor | Concentration (ng/mL) |
|---|---|
| PDGF-BB | 0.720 |
| bFGF | 0.019 |
| TGF-β1 | 5.92 |

For comparison purposes TGF-β1 levels in lyophilized PRP were compared to those obtained for basal PRP (no-activated) and PRP activated with $CaCl_2$ (Table 3). The PRP obtained before lyophilization was activated by mixing 1 ml of PRP with 50 µl 10% $CaCl_2$. After the PRP has gelled, samples were centrifuged at room temperature for 10 minutes at 4000 g and the supernatant was collected. A fraction of $CaCl_2$ activated supernatant was used to quantify TGF-β1.

TABLE 3

TGF-β1 levels (ng/mL)

|  | Non-activated | Activated with $CaCl_2$ |
|---|---|---|
| PRP | 3.7 ± 0.6 | 18.3 ± 4.4 |
| Lyophilized PRP | 15.3 ± 4.1 | 13.4 ± 3.9 |

The mechanical stress during the lyophilization process causes activation and release of grow factors, therefore addition of activators such as $CaCl_2$ is not necessary to release grow factors.

Example 2

Oral Composition

The PRP obtained was formulated according to the following composition obtaining a powder to be used as a solid formulation which can be suspended in water.

| PRP | 10.2% |
|---|---|
| Fructose | 76.0% |
| Mannitol | 10.2% |
| Pineapple flavour | 2.5% |
| Sodium ascorbate | 0.9% |
| Aerosil 200 | 0.15% |

Example 3

Tablet Oral Composition

The lyophilized PRP obtained as described in example 1 was formulated according to the following composition to obtain a tablet.

| PRP | 25.0% |
|---|---|
| Hydroxypropylcellulose | 2.0% |
| Sodium starch | 4.0% |
| Colloidal silica | 0.5% |
| Lactose monohydrate | 15.0% |
| Magnesium stearate | 1.2% |
| Microcrystalline cellulose | 52.3% |

Example 4

Capsules

The PRP obtained as described in example 1 was formulated according to the following composition to obtain a capsule.

| PRP | 15.0% |
|---|---|
| Mannitol | 15.0% |
| Sodium croscarmellose | 4.5% |
| Colloidal silica | 0.5% |
| Microcrystalline cellulose | 25.0% |
| Tricalcium phosphate | 40.0% |

Example 5

Treatment Evaluation

The composition described in Example 2 was administered orally to 20 patients with class II-Ill (ACR score) knee osteoarthritis. Patients were administered one dose daily for one month. Clinical outcomes related to joint function and pain were measured using VAS and WOMAC scales. The intake of rescue medication (analgesics/antiinflammatories) was registered. In addition, the subjective opinion in terms of efficacy and tolerability by physician and patient was analyzed. All the clinical outcomes were measured on day 0, 15, 30 and 60 (visits 1, 2, 3 and 4 respectively).

Descriptive statistics, mean, standard deviation and 95% confidence interval was calculated for all quantitative variables. Qualitative variables were analyzed by contingency tables and bar charts.

Differences between groups were analyzed by ANOVA for repeated measures with Bonferroni correction taking the first visit as a control for VAS and WOMAC scales.

Figure 2:
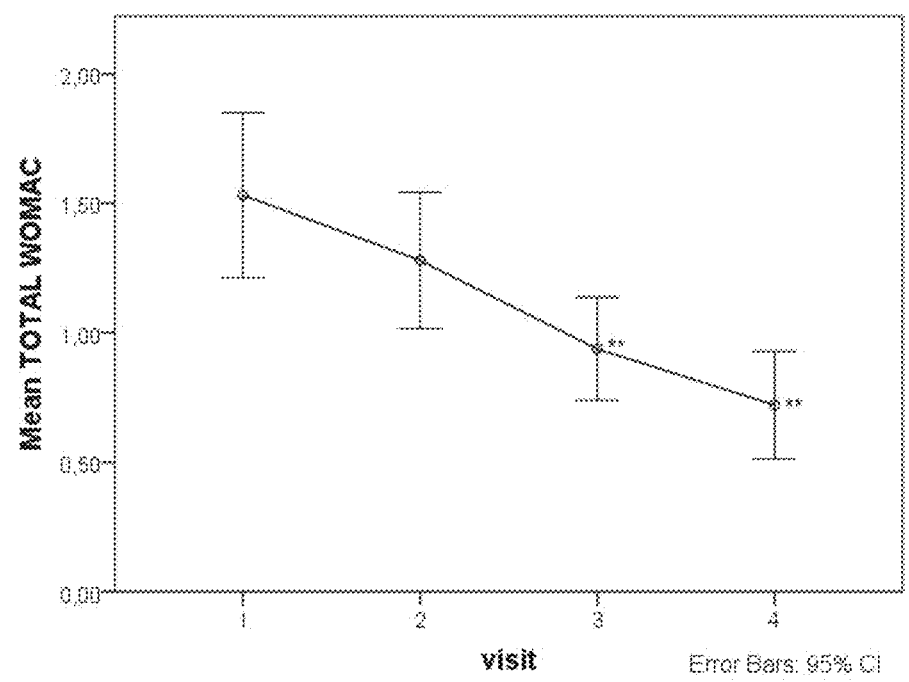
FIG. 2 shows mean WOMAC TOTAL scores at visits 1, 2, 3 and 4, which correspond to day 0, 15, 30 and 60 respectively. (Error bars 95% CI, ** $p<0.01$).

A statistically significant decrease in VAS pain score is observed from visit 2 (day 15) onwards (FIG. 1). Similarly, total WOMAC index (FIG. 2), which is related to the worsening of the quality of life due to osteoarthritis, is significantly reduced from visit 2 (day 15) onwards.

Figure 3:
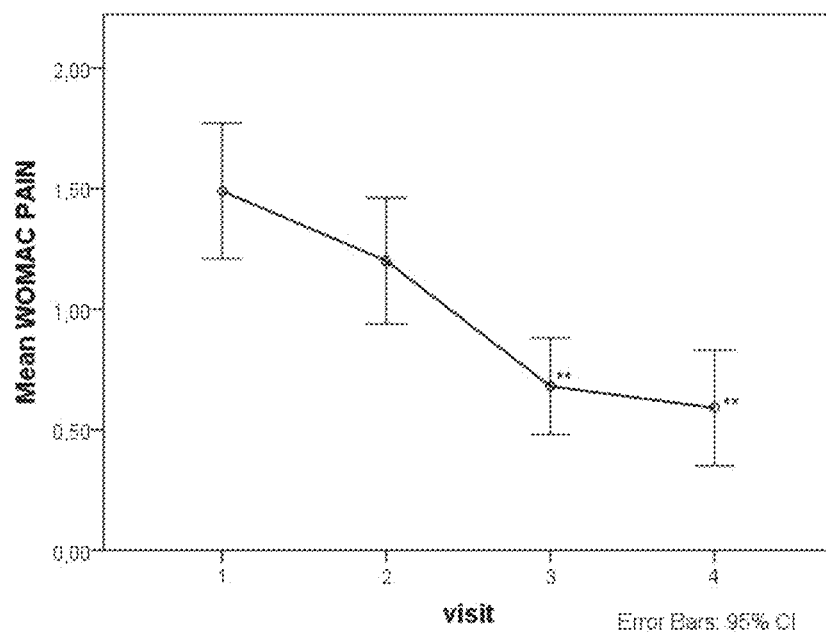
FIG. 3 shows mean WOMAC PAIN scores at visits 1, 2, 3 and 4, which correspond to day 0, 15, 30 and 60, respectively. (Error bars 95% CI, ** $p<0.05$).
Figure 4:
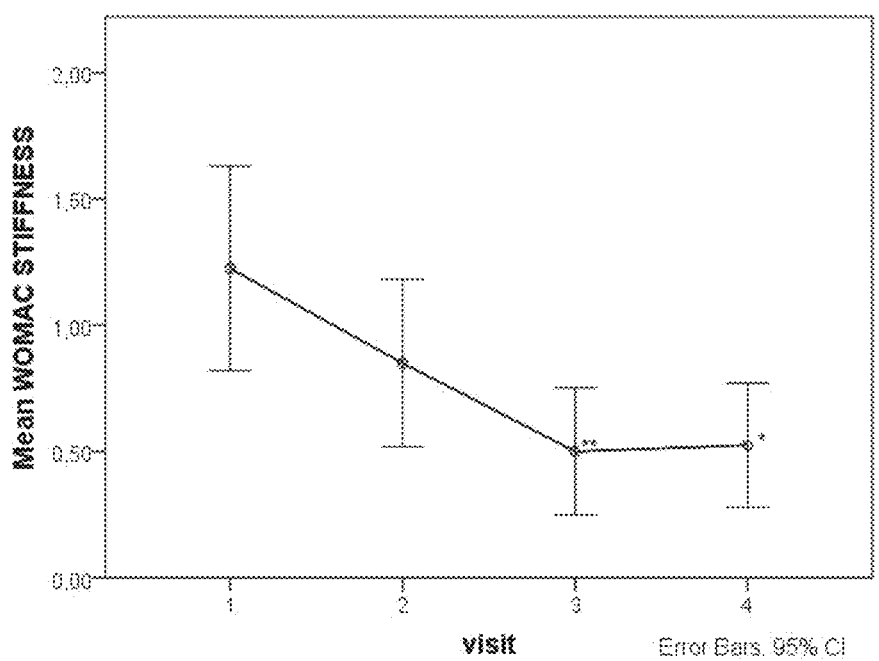
FIG. 4 shows mean WOMAC STIFFNESS scores at visits 1, 2, 3 and 4, which correspond to day 0, 15, 30 and 60, respectively. (Error bars 95% CI, * $p<0.05$; ** $p<0.01$).
Figure 5:
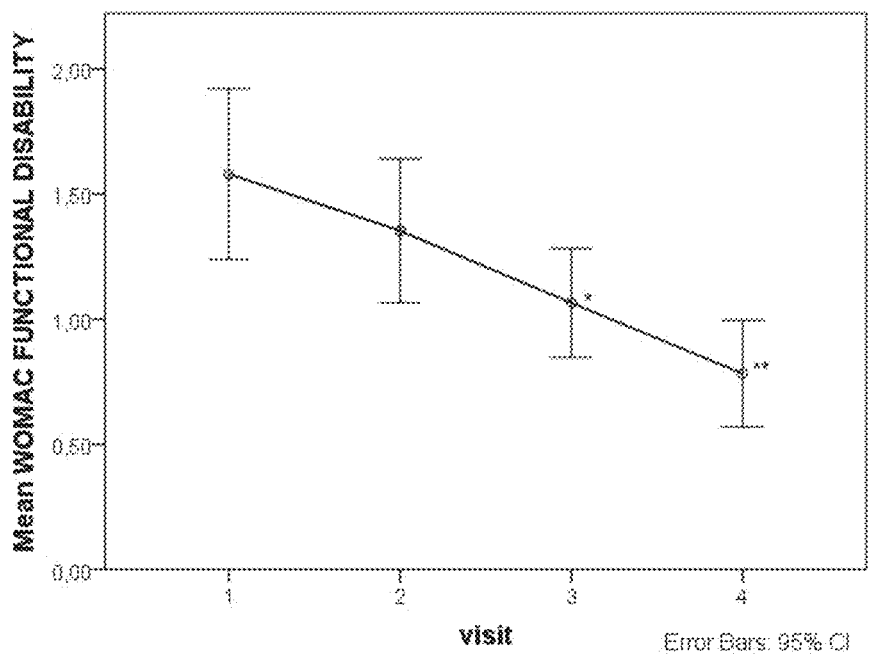
FIG. 5 shows mean WOMAC FUNCTIONAL DISABILITY scores at visits 1, 2, 3 and 4, which correspond to day 0, 15, 30 and 60, respectively. (Error bars 95% CI, * $p<0.05$; ** $p<0.01$).

The study of the individual components of the WOMAC scale (pain, stiffness and function) reveals a decrease in pain (FIG. 3), stiffness (FIG. 4) and functional disability (FIG. 5) scores, being significantly different from basal scores on visit 3 onwards.

Figure 6:
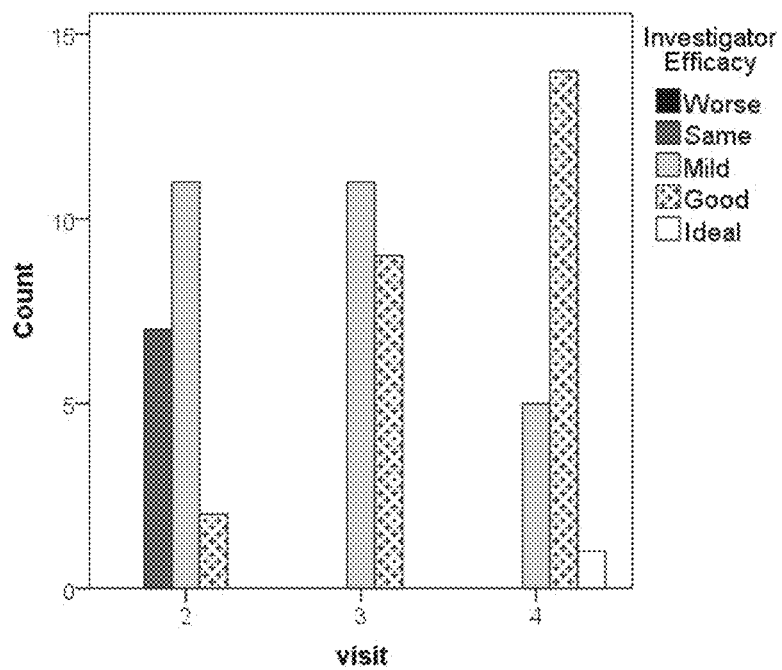
FIG. 6 shows subjective efficacy evaluation according to the physician at visits 2, 3 and 4 corresponding to day 15, 30 and 60 respectively.
Figure 7:
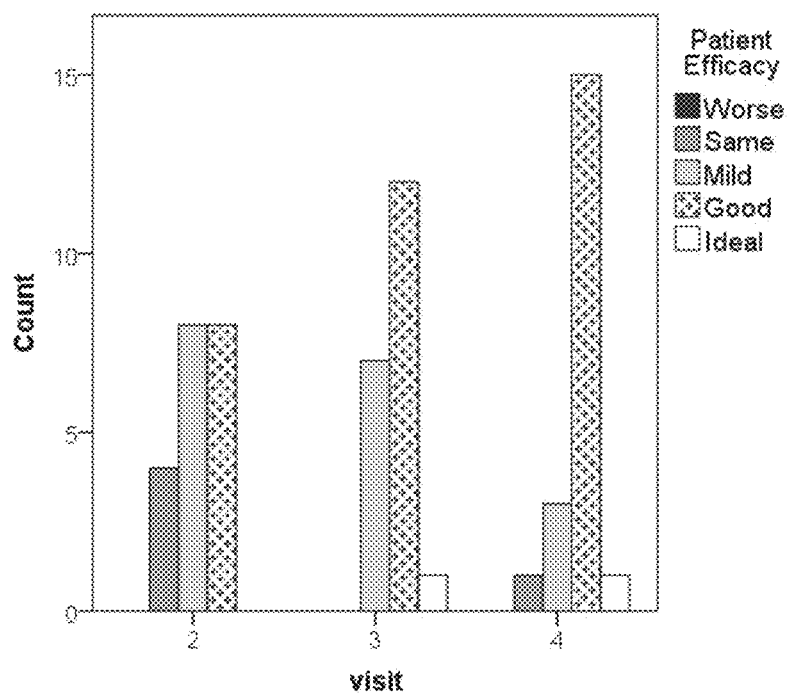
FIG. 7 shows subjective efficacy evaluation according to the patient. Visits 2, 3 and 4 correspond to days 15, 30 and 60 respectively.

Subjective efficacy according to physician was slightly effective or effective according to 65% of physicians and was good or slightly effective for 80% of patients on visit 2 (day 15). After 30 days, 100% of physicians considered the treatment good or slightly effective and 65% of patients considered the treatment good or ideal (Table 4 and 5, FIGS. 6 and 7). At the end of the study, 75% of the physicians and 80% of the patients considered the efficacy good or ideal.

Figure 8:
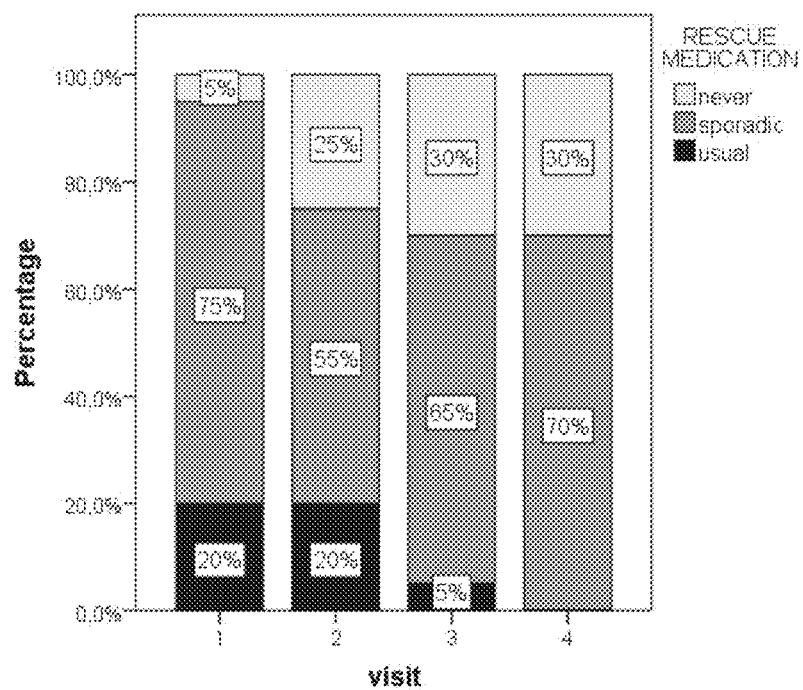
FIG. 8 shows the rescue medication intake evaluation. Visits 1, 2, 3 and 4 correspond to days 0, 15, 30 and 60 respectively.

Rescue medication intake was decreased throughout the advance of the study. The percentage of patients that took frequently analgesics/antiinflammatories was 20% at the beginning of the study, and negligible at the end (FIG. 8).

In the evaluation of tolerability throughout the study, 100% of the physicians and 95% of patients considered the tolerability good or excellent. No adverse events were registered (Table 6 and 7).

TABLE 4

Subjective efficacy according to the physician.

|  |  | No effect | | Slight efficacy | | Good efficacy | | Ideal efficacy | | |
|---|---|---|---|---|---|---|---|---|---|---|
|  |  | N | % within visit | N | % within visit | N | % within visit | N | % within visit | N total |
| visit | 2 | 7 | 35% | 11 | 55% | 2 | 10% | 0 | 0% | 20 |
|  | 3 | 0 | 0% | 11 | 55% | 9 | 45% | 0 | 0% | 20 |
|  | 4 | 0 | 0% | 5 | 25% | 14 | 70% | 1 | 5% | 20 |

TABLE 5

Subjective efficacy according to the patient.

|  |  | No effect | | Slight efficacy | | Good efficacy | | Ideal efficacy | | |
|---|---|---|---|---|---|---|---|---|---|---|
|  |  | N | % within visit | N | % within visit | N | % within visit | N | % within visit | N total |
| visit | 2 | 4 | 20% | 8 | 40% | 8 | 50% | 0 | 0% | 20 |
|  | 3 | 0 | 0% | 7 | 35% | 12 | 50% | 1 | 5% | 20 |
|  | 4 | 1 | 5% | 3 | 15% | 15 | 75% | 1 | 5% | 20 |

TABLE 6

Subjective tolerability evaluation according to the physician.

|  |  | Good and excellent | | |
|---|---|---|---|---|
|  |  | N | % within visit | N total |
| visit | 2 | 20 | 100% | 20 |
|  | 3 | 20 | 100% | 20 |
|  | 4 | 20 | 100% | 20 |

TABLE 7

Subjective tolerability evaluation according to the patient.

|  |  | Good and excellent | | |
|---|---|---|---|---|
|  |  | N | % within visit | N total |
| visit | 2 | 20 | 100% | 20 |
|  | 3 | 19 | 95% | 20 |
|  | 4 | 19 | 95% | 20 |

The invention claimed is:

1. A method of treating functional disability and/or pain associated with disorders or injuries selected from the group consisting of joint damage, injured tendons, arthritis, osteochondral lesions, tenosynovitis, bursitis, and ligament injuries in a subject in need thereof comprising:
orally administering an effective amount of a composition comprising heterologous platelet-rich plasma (PRP) to the subject, wherein the composition is swallowed;
wherein a statistically significant reduction in joint pain as measured using the VAS scale occurs after administration of the composition and/or a statistically significant improvement in pain, stiffness and function as measured using the WOMAC scale occurs after administration of the composition, and wherein the PRP has not been chemically activated.

2. The method according to claim 1, wherein the disorder or injury is osteoarthritis.

3. The method according to claim 1, wherein the heterologous platelet-rich plasma is of porcine origin.

4. The method according to claim 3, wherein the composition further comprises growth factors.

5. The method according to claim 4, wherein the growth factors are selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof.

6. The method according to claim 5, wherein the growth factors are transforming growth factors (TGF), platelet-derived growth factors (PDGF), fibroblast growth factor (FGF) or mixtures thereof.

7. The method according to claim 6, wherein the growth factors are transforming growth factors β (TGF-β), platelet-derived growth factors BB (PDGF-BB), basic fibroblast growth factors (bFGF) or mixtures thereof.

8. The method according to claim 7, wherein the growth factors are transforming growth factors β (TGF-β).

9. The method according to claim 8, wherein the growth factors are transforming growth factors β1 (TGF-β1).

10. The method according to claim 1, wherein the heterologous platelet-rich plasma is in solid form.

11. The method according to claim 1, wherein the composition is in the form of granules, tablet, suspension in a liquid carrier, capsule or powder.

12. The method according to claim 1, wherein the composition comprises:
a) between 1 and 25 wt % of heterologous platelet-rich plasma (PRP),
b) between 1 and 25 wt % of a bulking agent, and
c) between 50 and 98 wt % of at least one excipient or carrier.

13. The method according to claim 1, wherein the PRP is dried PRP.

14. The method according to claim 1, wherein the disorder or injury is tendonitis.

* * * * *